United States Patent [19]

Nishijima et al.

[11] Patent Number: 5,092,846
[45] Date of Patent: Mar. 3, 1992

[54] INTRODUCER FOR MEDICAL TUBE

[75] Inventors: Mamoru Nishijima, Machida; Fumiki Ura; Yasunobu Izumi, both of Yokohama, all of Japan

[73] Assignee: Sumitomo Bakelite Company Limited, Tokyo, Japan

[21] Appl. No.: 609,853

[22] Filed: Nov. 7, 1990

[30] Foreign Application Priority Data

Nov. 7, 1989 [JP] Japan .................................. 1-287805
Nov. 13, 1989 [JP] Japan ............................. 1-131045[U]

[51] Int. Cl.⁵ .......................................... A61M 5/178
[52] U.S. Cl. .................................. 604/165; 604/167
[58] Field of Search ............... 604/165, 164, 166, 167, 604/159, 256

[56] References Cited

U.S. PATENT DOCUMENTS

| | | | |
|---|---|---|---|
| 4,629,450 | 12/1986 | Suzuki et al. | 604/167 |
| 4,682,981 | 7/1987 | Suzuki et al. | 604/165 |
| 4,755,173 | 7/1988 | Konopka et al. | 604/167 |

FOREIGN PATENT DOCUMENTS

| | | |
|---|---|---|
| 60-88562 | 5/1985 | Japan . |
| 234671 | 11/1985 | Japan . |
| 61-45774 | 3/1986 | Japan . |
| 154679 | 7/1986 | Japan . |
| 2-5431 | 2/1990 | Japan . |

Primary Examiner—John J. Wilson
Attorney, Agent, or Firm—Browdy and Neimark

[57] ABSTRACT

A medical tube introducer comprising a body having a valve means encased in an inner cavity I, to which a sheath tube connected with the inner cavity I is mounted at the tip, and having a concave or convex portion formed at the center of the rear end and plural concave or convex portions around the center; and a grip member having an inner cavity II and a dilater at the tip portion which is connected with the inner cavity II and is capable of inserting into the inner cavity of the sheath tube in close contact with the inner cavity, and having a convex or concave portion formed at the positions corresponding to the concave or convex portion at the rear end of the body; said valve means being constructed with plural plate-like valve members, each of which valve members has plural slits crossing with each other at the center, and plural of valve members adjacent to each other are overlaid and integrally joined with each other by shifting the positions of said slits except for joining the slits at the center. The medical tube introducer can ensure fitting of the dilator member with the sheath member stably and hence can operate the sheath member simultaneously merely by operating the dilator member and ensures easy catheterization, i.e., insertion of catheters into a blood vessel, safely with a certainty.

6 Claims, 4 Drawing Sheets

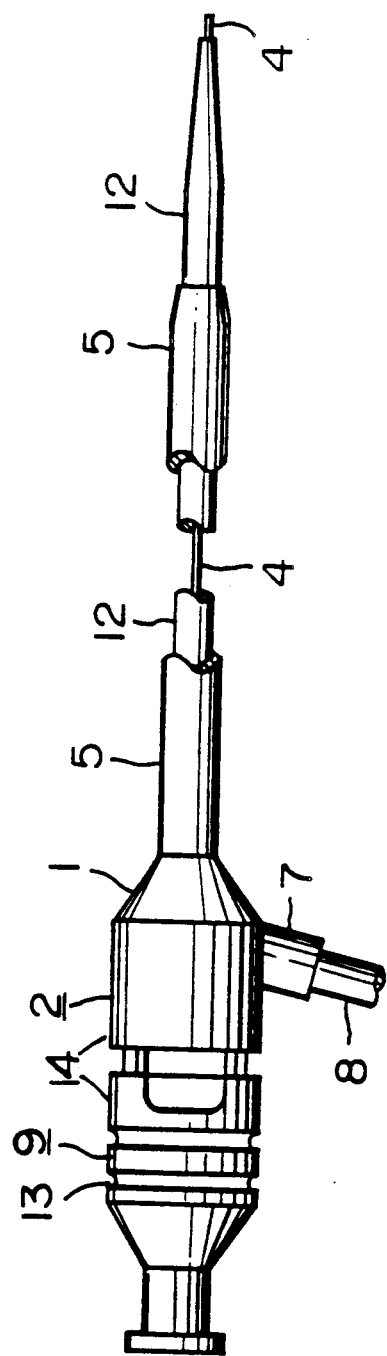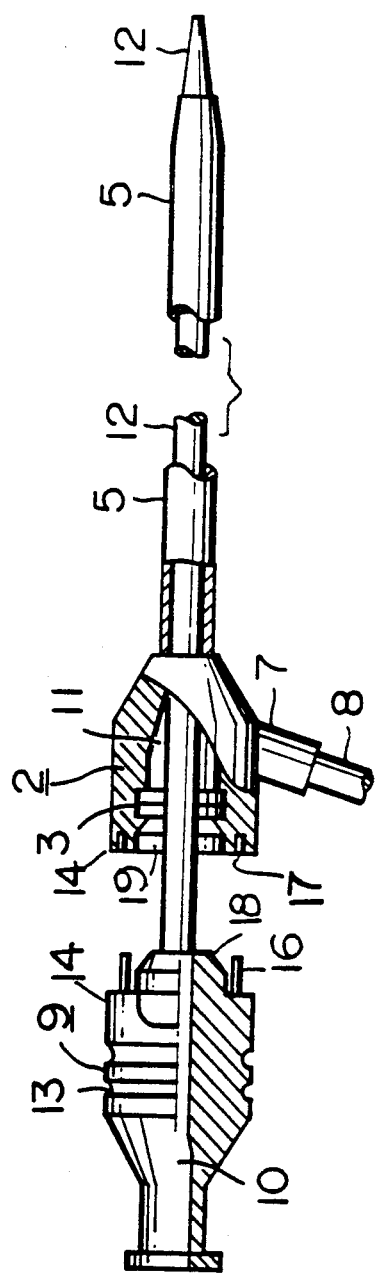
FIG. 1A
FIG. 1B

FIG. IC
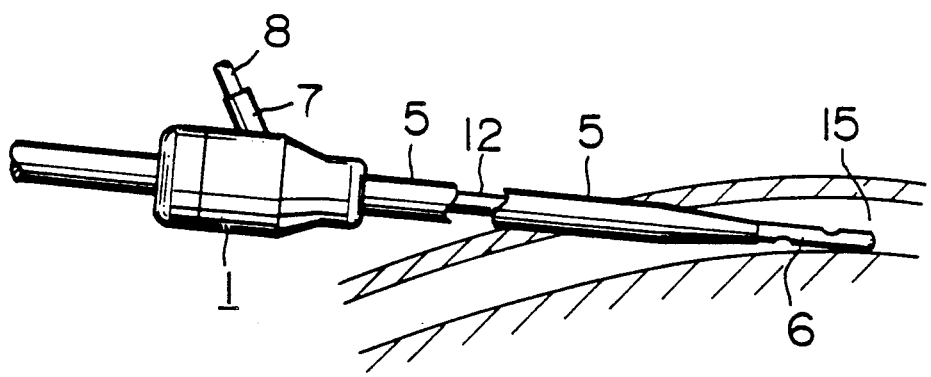
FIG. 2A
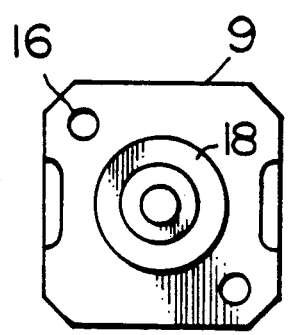
FIG. 2B
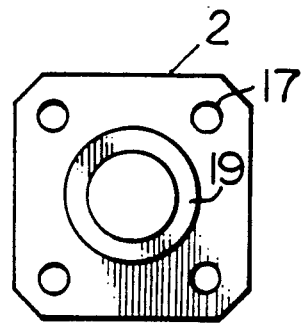
FIG. 3A
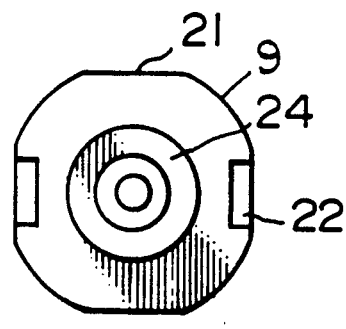
FIG. 3B
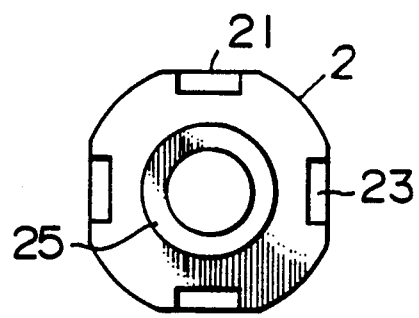

INTRODUCER FOR MEDICAL TUBE

BACKGROUND OF THE INVENTION

1. Field of the Invention

The present invention relates to a device for safely introducing catheters into a blood vessel, organs, etc. with certainty.

2. Description of the Related Art

Upon introduction of catheters into the body for purposes of diagnosis or treatment, especially upon insertion of a vascular balloon catheter, a catheter for angiography or a catheter with a sensor for detecting temperature, pH, oxygen, etc. into a blood vessel, safe and sure handling is required Seldinger's method has been widely adopted, as a method using a device as an auxiliary means for percutaneously introducing vascular catheters into a blood vessel. The basic technique of this method comprises percutaneously inserting a hollow stylus with an inner needle through the skin to thereby introduce the stylus into a blood vessel, withdrawing the inner needle from the hollow stylus, then inserting a guide wire into the hollow stylus, withdrawing the hollow stylus to keep the guide wire alone in the blood vessel, and then inserting into a blood vessel a catheter having an opening at the tip and the end, along the guide wire.

In addition, a method using an introducer for medical tube has also been widely used, by applying the basic technique of Seldinger's method described above. This method comprises first inserting a guide wire into a blood vessel according to the Seldinger's method, next sliding an introducer coupled with a dilator into the blood vessel along the guide wire to keep the introducer in the blood vessel, and guiding the catheter along the guide path of the introducer thereby resulting in insertion of the catheter into the blood vessel.

The conventional prior art introduced as shown in FIG. 6A and B is constructed with a body (2), an end cap (43) and a valve means (64) composed of a resilient material to avoid bloodstream leaking. The catheter is slid and penetrated through body (2) of introducer (1) via valve means (64), whereby reflux or leakage of blood is prevented. However, when blood pressure is high for some reason or valve means (64) does not instantaneously close following sudden withdrawal of catheter (65), blood may leak out.

In the conventional prior art introducer, the dilator member is generally inserted and fitted into the inner cavity of a sheath member. However, stability in connection of the two members and operability has not been sufficient.

For example, in a medical device disclosed in Japanese Patent Application. No. 59-165452 (Japanese Patent Application Laid-Open No. 61-45774), as a means for preventing a relative motion in the dilator member and the sheath member, there is disclosed a structure in which only a concave portion and the convex portion are provided. Such a structure can prevent relative movement between both members in an axial direction and in a rotating direction but involves a drawback that stability in connection or operability is insufficient. That is, it is difficult to operate the dilator member when engaged to the sheath member because it is necessary to firmly hold the members which is a distraction during operation of the introducer. This is particularly a problem in catheterization while rotating a catheter or doing precise operations because so much attention must be directed to maintaining stability between the dilator and the sheath.

As described above, conventional catheter introducers involve complicated operations which require careful handling. Thus, there is a fear that trauma may occur upon insertion of a catheter into a blood vessel with prior art introducers.

In order to overcome these problems, prior art catheters such as shown in FIG. 7 have been developed in which a first valve member (76) is overlaid on a second valve member (77) to construct a valve means (64) and slits (62) provided respectively are in agreement at the central portion but other positions are staggered with each other thereby to enhance a liquid sealing effect around the dilator. This type of device is shown in (Japanese Patent Application No. 58-196950 (Japanese Patent Application Laid-Open No. 60-88562), Japanese Patent Application No. 59-281077 (Japanese Patent Application Laid Open No. 61-154679) and Japanese Patent Application No. 59-90890 (Japanese Patent Application Laid-Open No. 60-234671).

When a catheter with a small diameter not closely fitted to a catheter tube is used or a guide wire alone is inserted with the prior art introducers, these devices are not always successful in preventing a reflux of bloodstream or leakage of blood. In addition, the valve members are merely overlaid on each other and not integrally joined and hence, a problem of stability between the dilator and the sheath is created.

OBJECT AND SUMMARY OF THE INVENTION

An object of the present invention is to provide a catheter introducer for medical use in which the dilator member is securely fitted with the sheath member so that the sheath member can be simultaneously operated with the dilator member and permit insertion of a catheter safely into a blood vessel with certainty.

The medical introducer of the present invention comprises a body having a valve means encased in a first inner cavity, to which a sheath tube communicating with the first inner cavity is mounted at the tip. The body has a concave portion or a convex portion formed at the center of the rear end and a plurality of bores or rod connectors around the center. The introducer further comprises a grip member having a second inner cavity and a dilator with a tip portion which is connected with the second inner cavity and is capable of insertion through the first inner cavity of the sheath tube in close contact with the inner cavity. The grip member also has a convex portion and/or a concave portion formed at the positions corresponding to the concave portion and/or convex portion at the rear end of the body.

The introducer further has valve means consisting of a plurality of plate-like valve members. Each valve member has one or a plurality of slits which cross at the center and, a plurality of valve members adjacent to each other are overlaid so as to be staggered and integrally joined except that the slits fit well with each other at the center. Preferably, a concave portion is formed on the outer surface of the valve member disposed at the rear end.

BRIEF DESCRIPTION OF THE DRAWINGS

FIG. 1A shows a full view of the catheter introducer of the invention with a body integrally fitted to a grip member, FIG. 1B is a partially cross-sectioned view showing the body and the grip member separated from each other, FIG. 1C shows a sheath tube at the tip of the introducer inserted into a blood vessel under the skin with a catheter tube further introduced therein, FIG. 2A shows one embodiment of the forward end surface of the grip member, FIG. 2B shows the rear end of the body which cooperates with the end surface of FIG. 2A, FIG. 3A shows a view similar to FIG. 2A of a second embodiment of the forward end of the grip member, FIG. 3B shows the rear end of the body which cooperates with the end surface of FIG. 3A.

DESCRIPTION OF THE PREFERRED EMBODIMENT

Figure 4:
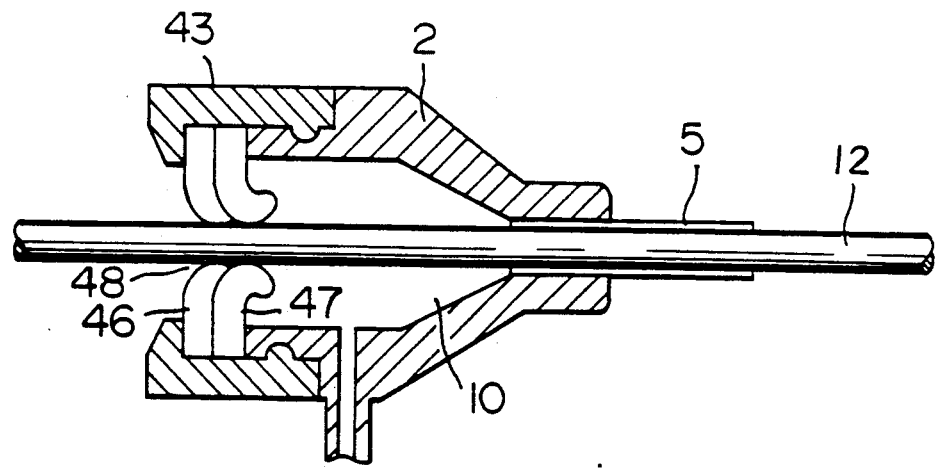
FIG. 4 is a cross-sectional view of another embodiment of the invention showing a catheter tube inserted into the introducer.

Hereinafter the catheter introducer of the present invention is described in detail with reference to the drawings.

FIG. 1A and B shows the catheter introducer of the present invention, wherein FIG. 1A represents an assembled view of the introducer comprising a body integrally fitted to a grip member, and FIG. 1B is a disassembled view of the body and the grip member. The body (2) has an inner cavity (11) which encases valve means (3) therein. A sheath tube (5) is connected to the tip of body (2) so that the interior of tube (5) communicates with inner cavity (11). In addition, the body (2) has a branching member (7) which is connected with a three-way stockcock via a connecting tube (8), through which heparinated saline or the like may be infused.

The grip member (9) which can be engaged to body (2) has an inner cavity (10). A dilator (12) which passes through the inner cavity (10), is connected to the grip member at the tip portion thereof. A groove (13) or the like is provided around the grip member 9 for easy holding. The rear end portion of grip (9) is formed with a general-purpose connector which is convenient for connection with and insertion of a syringe, etc..

FIGS. 2A and 2B show an embodiment of the fitting area (14) of the body (2) and the grip member (9), wherein FIG. 2A indicates the forward end surface of the grip member (9) and FIG. 2B indicates the rear end surface of the body (2). The fitting area (14) of the grip member (9) and the body (2) is substantially rectangular in cross section to provide an easily holdable shape. The forward end surface of the grip member (9) has a convex portion (18) at the central portion and two connecting pins (16) on the diagonal line thereto. Corresponding to convex portion (18) and connecting pins (16), the rear end surface of the body (2) has the concave portion (19) at the central portion and four bores (17) on the diagonal line crossing with each other which can receive connecting pins (16) and convex portion (18). The number of corresponding connecting pins (16) and bore (17) are not necessarily limited to that shown in FIGS. 2A and 2B. For the sake of interchangeability, however, the illustrated embodiment is preferred because fitting can be effected without consideration of length or crosswise directional properties.

FIG. 3A and B show another embodiment of the fitting area (14) of the body (2) and the grip member (9), wherein FIG. 3A indicates the forward end surface of the grip member (9) and FIG. 3B indicates the rear end surface of the body (2). The fitting area (14) of the grip member (9) and the body (2) is substantially circular in cross section with four flat portions (21) on the diagonal line to facilitate holding and rotating the catheter introducer. The forward end surface of the grip member (9) has the convex portion (24) at the central portion and two connecting pins (22), on the left and right ends or at the upper and lower ends. Corresponding to the convex portion (24) and connecting pins (22) the rear end surface of the body (2) has a concave portion (25) at the central portion and four slots (23) which can receive connector pins (22) so that they are fittable with each other without consideration of length or crosswise directional properties.

In the embodiments illustrated in FIGS. 2A, 2B, 3A and 3B, the concave portion is provided on the rear end side of the body (2) and the connecting pins and the convex portions are provided on the forward end side of the grip member (9). Alternatively, all the engaging elements (connecting pins, bores or slots, concave and convex portions) can be reversed on body (2) and grip member (9). These embodiments are within the category of the present invention.

Figure 5A:
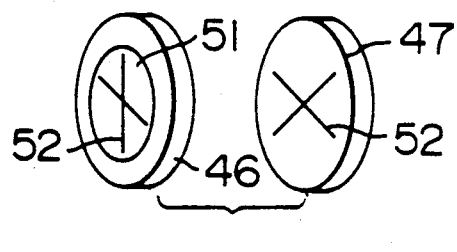
FIG. 5 shows an embodiment of valve means in the introducer according to the present invention.
Figure 5B:
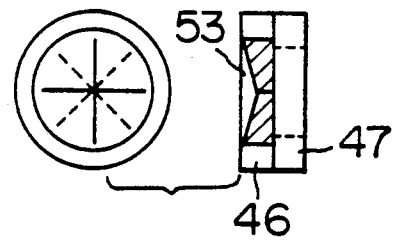
Figure 7:
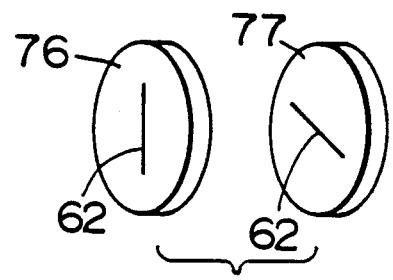
FIG. 7 shows the prior art valve means of the introducer of FIG. 6A and 6B.
Figure 6A:
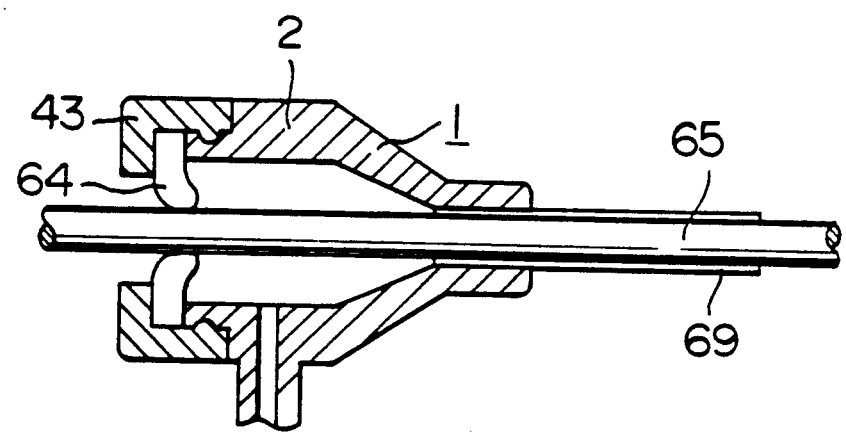
FIG. 6A shows an assembled structure of a conventional prior art introducer.
Figure 6B:
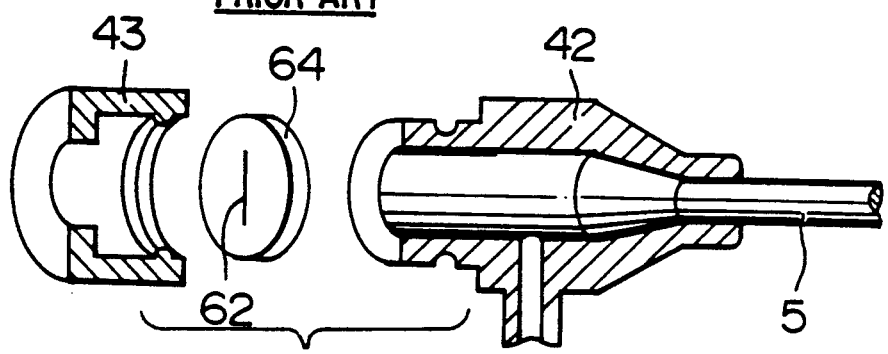
FIG. 6B shows the introducer of FIG. 6A disassembled.

As can be seen from FIGS. 4 and 5A the valve member constituting the valve means (3) of the present invention could be made as a single element or may be constructed as shown in FIGS. 4 and 5B generally with a plurality of valve members (46) and (47), each of which valve members has one or more, and preferably 2 or 3 slits (52) to maintain their liquid sealing property and make insertion of dilator (12) easier. It is advantageous that a length of slits (52) be 1.2 times or more, preferably about 1.5 to about 3 times the diameter of the catheter (4), in view of the ultimate insertion and need to seal around the catheter (4). As shown in FIG. 5B, a concave portion (53) which forms a concavity or a conical depression toward the center is provided on the outer surface of the first valve member (46) disposed at the rear end side of the body (2), whereby the catheter (4) can be readily inserted.

The sealing effect and the holding of dilator (12) can be greatly enhanced by shifting the positions of the slits (52) except for joining and putting the slits together at the center, as illustrated the FIG. 5A and B. Movement of the inserted dilator member (12) through the slits of the valve member (46) and the valve member (47) is restrained by the valve members so that the grip member is firmly held to the body.

The number of valve members that can be used varies depending on a thickness of one valve member but may be suitably 2 to 4 members. Further by integrally joining the surfaces of the respective valve members overlaid adjacent to each other with an adhesive, or self-adhesive, the liquid sealing property and dilator holding property can be more improved. The members may also be integrally joined using a repellant.

The valve member (3) is composed of a soft resilient material such as synthetic rubbers, e.g., silicone rubber, fluororubber, polybutadiene, natural rubber, thermoplastic elastomer, etc..

Next, the method for introducing a medical tube with the introducer in accordance with the present invention is explained below with reference to FIG. 1.

Firstly, a hollow stylus with an inner needle is percutaneously inserted into a blood vessel; the inner needle is then withdrawn and a guide wire (4) is inserted into the hollow stylus, and the hollow stylus is withdrawn, whereby the guide wire (4) is retained in the blood vessel.

As is illustrated in FIG. 1A and B, a dilator (12) engaged to the introducer (1), is slid along the guide wire (4) while expanding the wall of the blood vessel (15) to introduce the sheath tube (5) of the introducer (1) into the blood vessel. Then, the dilator (12) and the guide wire (4) are withdrawn, while infusing heparinated saline into the inner cavity (11) via a feeding tube (8) connected with a branching member (7).

While the guide wire (4) and the dilator (12) are inserted in the introducer (1) as such, the valve means (3) seals the outer circumference of the dilator (12) to prevent a reflux and leakage of bloodstream. Even when a tube having a narrow diameter is used or only a guide wire (4) is inserted, a similar sealing effect is maintained. Further when the guide wire (4) and the dilator (12) are withdrawn, blood refluxed through the sheath tube (5) from the blood vessel is fully blocked by the valve means (3), whereby leakage of blood is prevented. Furthermore, when a catheter (6) according to the present invention is inserted, blood is prevented from leaking by close sealing with the valve means (3), irrespective of the size of tube.

By specifically designing the valve means, the medical tube introducer in accordance with the present invention ensures the liquid sealing property not only in the closed state in which the tubes are not inserted but also upon puncture of the tubes into the introducing portion. Regardless of size (diameter) of the tubes, the effect is not lost or lowered even in the case of using a narrow guide wire alone or even after rapid withdrawal of the tubes. Therefore, there is provided a simple introducer which can surely prevent blood from leaking and can be safely operated.

The medical tube introducer in accordance with the present invention can be inserted into a blood vessel easily, surely and safely in a united state of the dilator member and the sheath member without any shift, by inserting the introducer while grasping an appropriate site of the body, the grip member, etc. and suitably rotating the same upon sliding and inserting the introducer along the guide wire previously inserted in the blood vessel. The operator can thus concentrate on operations with less concern to handling of catheterization equipment. Therefore, the introducer of the present invention is exremely useful as a medical apparatus for catheterization.

As described above, the corresponding convex portion/concave portion are provided at the center of the forward end surface of the grip member in the introducer of the present invention, as a means for preventing a relative motion between the dilator member and the sheath member separately therefrom, connecting pins or bores/slots are provided around the convex portion/concave portion and the corresponding concave portion/concave portion are provided at the rear end surface of the body. Therefore, the relative movement between the dilator member and the sheath member in a lengthwise direction and in a rotating direction can be prevented more surely.

Furthermore in the introducer of the present invention, the valve members are overlaid and unitedly joined by shifting the positions of the slits, except for joining the slits of the valve members at the center so that the fitted and united dilator and sheath are held with certainty.

Further in the introducer of the present invention, the fitting structure of the forward end surface of the grip member and the rear end surface of the body cooperates with the structure of the valve means to unitedly join the grip member and the body. Thus, the grip member and the body can be integrally put together with an extremely certainty.

What is claimed is:

1. A medical tube introducer comprising a body having a rear end and a tip, and a valve means encased in an inner cavity I, to which a sheath tube connected with the inner cavity I is mounted at the tip, and having a concave portion formed at the center of the rear end and a plurality of concave portions around the center; and a grip member having an inner cavity II and a dilator at the tip portion which is connected with the inner cavity II and is capable of inserting into the inner cavity of the sheath tube in close contact with the inner cavity, and having a plurality of convex portions formed at the positions corresponding to the concave portions at the rear end of the body, the rear end of the body and the tip portion of the grip member having the same external complementary shape to provide four flat portions, thereby effecting easy fitting between the body and the grip.

2. A medical tube introducer as claimed in claim 1, wherein said valve means is constructed with a plurality of plate-like valve members, each of which valve members has a plurality of slits crossing with each other at the center, and a plurality of valve members adjacent to each other are overlaid and integrally joined with each other by shifting the positions of said slits except for joining the slits at the center.

3. A medical tube introducer as claimed in claim 1, wherein said valve member disposed at the rear end has a concave portion formed on an outer side thereof.

4. A medical tube introducer comprising a body having a rear end and a tip, and a valve means encased in an inner cavity I, to which a sheath tube connected with the inner cavity I, is mounted at the tip, and having a convex portion formed at the center of the rear end and a plurality of convex portions around the center; and a grip member having an inner cavity II and a dilator at the tip portion which is connected with the inner cavity II and is capable of inserting into the inner cavity of the sheath tube in close contact with the inner cavity, and having a plurality of concave portions formed at the positions corresponding to the convex portions at the rear end of the body, the rear end of the body and the tip portion of the grip member having the same external complementary shape to provide four flat portions, thereby effecting easy fitting between the body and the grip.

5. A medical tube introducer as claimed in claim 4, wherein said valve means is constructed with a plurality of plate-like valve members, each of which valve members has a plurality of slits crossing with each other at the center, and a plurality of valve members adjacent to each other are overlaid and integrally joined with each other by shifting the positions of said slits except for joining the slits at the center.

6. A medical tube introducer as claimed in claim 4, wherein said valve member disposed at the rear end has a concave portion formed on an outer side thereof.

* * * * *